United States Patent
MacDougall

(10) Patent No.: US 7,511,162 B2
(45) Date of Patent: Mar. 31, 2009

(54) PREPARATION OF AMINO ACID-FATTY ACID ANHYDRIDES

(75) Inventor: Joseph MacDougall, Mississauga (CA)

(73) Assignee: Multi Formulations Ltd., Mississauga, Ontario (CA)

( * ) Notice: Subject to any disclaimer, the term of this patent is extended or adjusted under 35 U.S.C. 154(b) by 90 days.

(21) Appl. No.: 11/747,203

(22) Filed: May 10, 2007

(65) Prior Publication Data

US 2008/0200725 A1 Aug. 21, 2008

Related U.S. Application Data

(63) Continuation-in-part of application No. 11/676,623, filed on Feb. 20, 2007, now Pat. No. 7,314,945.

(51) Int. Cl.
*C07C 101/00* (2006.01)

(52) U.S. Cl. .................................. 554/105

(58) Field of Classification Search .................. None
See application file for complete search history.

(56) References Cited

U.S. PATENT DOCUMENTS

| 3,024,272 | A | * | 3/1962 | Hyson et al. | ............... 562/562 |
| 5,994,581 | A | | 11/1999 | Fang | |
| 2004/0023889 | A1 | | 2/2004 | Gardiner et al. | |

FOREIGN PATENT DOCUMENTS

| CA | 1022849 | | 12/1977 |
| CA | 2577439 | A1 | 5/2007 |
| EP | 0339498 | | 11/1989 |
| WO | 03/099806 | A1 | 12/2003 |
| WO | 03/101402 | A2 | 12/2003 |
| WO | 2006/081682 | A1 | 8/2006 |

OTHER PUBLICATIONS

Harris RC, et al. Elevation of creatine in resting and exercised muscle of normal subjects by creatine supplementation. Clin Sci (Lond). Sep. 1992;83(3):367-74.

Greenhaff PL, et al. Effect of oral creatine supplementation on skeletal muscle phosphocreatine resynthesis, Am J Physiol. May 1994;266(5 Pt 1):E725-30.

Greenhaff PL, et al. Influence of oral creatine supplementation of muscle torque during repeated bouts of maximal voluntary exercise in man. Clin Sci (Lond). May 1993;84(5):565-71.

Olsen S, et al. Creatine supplementation augments the increase in satellite cell and myonuclei number in human skeletal muscle induced by strength training. J Physiol. Jun. 2006;573(Pt 2):525-34.

Zammit PS, et al. The Skeletal Muscle Satellite Cell: The Stem Cell That Came In From the Cold. J Histochem Cytochem. Aug. 2006; 54(11):1177-91.

Sartorelli V, et al. Molecular and cellular determinants of skeletal muscle atropy and hypertropy Sci STKE Jul. 2004;(244):re11.

Willaims MH, et al. Creatine supplementation and exercise performance: an update. J Am Coll Nutr. Jun. 1998:17(3):216-34.

Dox AW, et al. Esterification of creatine. J Biol Chem. 1922;67:671-73.

PCT/CA2007/000257 International Search Report, International Filing Date: Feb. 20, 2007, Applicant Multi Formulations Ltd. et al., date mailed: Jul. 18, 2007.

PCT International Search Report, PCT/CA2007/001640, International Filing date: Sep. 14, 2007, Applicant: Multi Formulations Ltd. et al.

PCT International Search Report, PCT/CA2007/000810, International Filing date: May 10, 2007, Applicant: Multi Formulations Ltd. et al.

Kretschmayer, R. and Jesserer, H. Biochemische Zeitschrift, 1937, 292(403-418), 419-423.

Tazawa, Y. Acta Phytochim. (Japan) 1935, 8, 331-336.

* cited by examiner

*Primary Examiner*—Deborah D. Carr
(74) *Attorney, Agent, or Firm*—Torys LLP

(57) ABSTRACT

The present invention describes compounds produced from an amino acid molecule and a fatty acid molecule. The compounds being in the form of amino-fatty acid compounds being bound by an anhydride linkage, or mixtures thereof made by reacting amino acids or derivatives thereof with an appropriate fatty acid previously reacted with a thionyl halide. The administration of such molecules provides supplemental amino acids with enhanced bioavailability and the additional benefits conferred by the specific fatty acid.

23 Claims, No Drawings

PREPARATION OF AMINO ACID-FATTY ACID ANHYDRIDES

CROSS-REFERENCE TO RELATED APPLICATION

The present application is a Continuation-in-Part of U.S. patent application Ser. No. 11/676,623 entitled "Creatine-Fatty Acids," filed Feb. 20, 2007, now U.S. Pat. No. 7,314,945 and claims benefit of priority thereto; the disclosure of which is hereby fully incorporated by reference.

FIELD OF THE INVENTION

The present invention relates to structures and synthesis of amino acid-fatty acid compounds bound via an anhydride linkage. Specifically, the present invention relates to a compound comprising an amino acid bound to a fatty acid, wherein the fatty acid is preferably a saturated fatty acid and bound to the amino acid via an anhydride linkage.

BACKGROUND OF THE INVENTION

Participation in sports at any level either professional or amateur requires an athlete to strive to bring their bodies to a physical state which is considered optimum for the sport of interest. One of the factors that correlate positively with successful participation in a sport is a high degree of development of the aerobic capacity and/or strength of skeletal muscle. Consequently, it is important that nutrients and other requirements of muscles be readily available and that they be transported to areas where they are needed without obstructions.

Strength and aerobic capacity are both functions of training and of muscle mass. As such, an athlete who can train harder and longer is often considered to be the most effective at participation in the sport of interest. Strenuous exercise is an effective stimulus for protein synthesis. However, muscle requires a large array of nutrients, including amino acids, in order to facilitate this increased level of protein synthesis.

Following periods of strenuous exercise, muscle tissue enters a stage of rapid nitrogen absorption in the form of amino acids and small peptides. This state of increased nitrogen absorption is a result of the body repairing exercise-induced muscle fiber damage as well as the growth and formation of new muscle fibers. It is important that muscles have sufficient levels of nitrogen, in the form of amino acids and small peptides, during this period of repair and growth. When an athlete is participating in a strenuous exercise regime and fails to ingest enough nitrogen, e.g. amino acids, the body often enters a state of negative nitrogen balance. A negative nitrogen balance is a state in which the body requires more nitrogen, to facilitate repair and growth of muscle, than is being ingested. This state causes the body to catabolize muscle in order to obtain the nitrogen required, and thus results in a decrease in muscle mass and/or attenuation of exercise-induced muscle growth. Therefore, it is important that athletes ingest adequate amounts of amino acids in order to minimize the catabolism of muscle in order to obtain the results desired from training.

Although supplementation with amino acids are quite common, the uptake of amino acids by cells is limited or slow since amino acid residues are not soluble or only slightly soluble in nonpolar organic solution, such as the lipid bilayer of cells. As a result amino acids must be transported into cells via transport mechanisms which are specific to the charges that the amino acid bears. It is therefore desirable to provide, for use in individuals, e.g. animals and humans, forms and derivatives of amino acids with improved characteristics that result in increased stability and increased uptake by cells. Furthermore, it would be advantageous to do so in a manner that provides additional functionality as compared to amino acids alone.

Fatty acids are carboxylic acids, often containing a long, unbranched chain of carbon atoms and are either saturated or unsaturated. Saturated fatty acids do not contain double bonds or other functional groups, but contain the maximum number of hydrogen atoms, with the exception of the carboxylic acid group. In contrast, unsaturated fatty acids contain one or more double bonds between adjacent carbon atoms, of the chains, in cis or trans configuration The human body can produce all but two of the fatty acids it requires, thus, essential fatty acids are fatty acids that must be obtained from food sources due to an inability of the body to synthesize them, yet are required for normal biological function. The fatty acids which are essential to humans are linoleic acid and α-linolenic acid.

Examples of saturated fatty acids include, but are not limited to myristic or tetradecanoic acid, palmitic or hexadecanoic acid, stearic or octadecanoic acid, arachidic or eicosanoic acid, behenic or docosanoic acid, butyric or butanoic acid, caproic or hexanoic acid, caprylic or octanoic acid, capric or decanoic acid, and lauric or dodecanoic acid, wherein the aforementioned comprise from at least 4 carbons to 22 carbons in the chain.

Examples of unsaturated fatty acids include, but are not limited to oleic acid, linoleic acid, linolenic acid, arachidonic acid, palmitoleic acid, eicosapentaenoic acid, docosahexaenoic acid and erucic acid, wherein the aforementioned comprise from at least 4 carbons to 22 carbons in the chain.

Fatty acids are capable of undergoing chemical reactions common to carboxylic acids. Of particular relevance to the present invention are the formation of anhydrides and the formation of esters.

SUMMARY OF THE INVENTION

In the present invention, compounds are disclosed, where the compounds comprise an amino acid bound to a fatty acid, via an anhydride linkage, and having a structure of Formula 1:

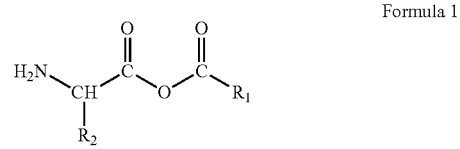

Formula 1 where:

R$_1$ is an alkyl group, preferably saturated, and containing from about 3 to a maximum of 21 carbons.

R$_2$ is hydrogen, methyl, isopropyl, isobutyl, sec butyl, acetylamide, propylamide, butyl-1-amine, or 1-butylguanidine.

Another aspect of the invention comprises the use of a saturated fatty acid in the production of compounds disclosed herein.

A further aspect of the present invention comprises the use of an unsaturated fatty in the production of compounds disclosed herein.

DETAILED DESCRIPTION OF THE INVENTION

In the following description, for the purposes of explanation, numerous specific details are set forth in order to provide a thorough understanding of the present invention. It will be apparent, however, to one skilled in the art that the present invention may be practiced without these specific details.

The present invention relates to structures and synthesis of amino acid-fatty acid compounds bound via an anhydride linkage. In addition, specific benefits are conferred by the particular fatty acid used to form the compounds in addition to, and separate from, the amino acid substituent.

As used herein, the term 'fatty acid' includes both saturated, i.e. an alkane chain as known in the art, having no double bonds between carbons of the chain and having the maximum number of hydrogen atoms, and unsaturated, i.e. an alkene or alkyne chain, having at least one double or alternatively triple bond between carbons of the chain, respectively, and further terminating the chain in a carboxylic acid as is commonly known in the art, wherein the hydrocarbon chain is greater than four carbon atoms. Furthermore, essential fatty acids are herein understood to be included by the term 'fatty acid'.

As used herein, "amino acid" refers a compound consisting of a carbon atom to which are attached a primary amino group, a carboxylic acid group, a side chain, and a hydrogen atom. For example, the term "amino acid" includes, but is not limited to, Glycine, Alanine, Valine, Leucine, Isoleucine, Asparagine, Glutamine, Lysine and Arginine. Additionally, as used herein, "amino acid" also includes derivatives of amino acids such as esters, and amides, and salts, as well as other derivatives, including derivatives having pharmacoproperties upon metabolism to an active form.

According to the present invention, the compounds disclosed herein comprise an amino acid bound to a fatty acid, wherein the fatty acid is preferably a saturated fatty acid. Furthermore, the amino acid and fatty acid are bound via an anhydride linkage and having a structure according to that of Formula 1. The aforementioned compound being prepared according to the reaction as set forth for the purposes of the description in Scheme 1:

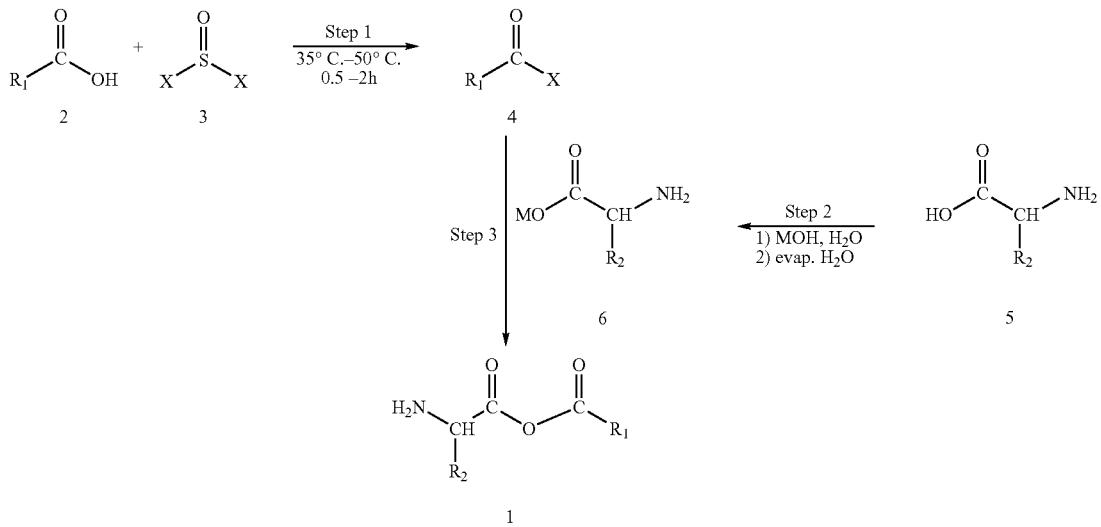

where:
$R_1$ = alkane or alkene (C = 3 to 21)
$R_2$ = hydrogen, methyl, isopropyl, isobutyl, sec butyl, acetylamide, propylamide, butyl-1-amine, and 1-butylguanidine
X = Cl, Br, F, or I
M = Na, K, Li, or $NH_4$ With reference to Scheme 1, in Step 1 an acyl halide (4) is produced via reaction of a fatty acid (2) with a thionyl halide (3).

In various embodiments of the present invention, the fatty acid of (2) is selected from the saturated fatty acid group comprising butyric or butanoic acid, caproic or hexanoic acid, caprylic or octanoic acid, capric or decanoic acid, lauric or dodecanoic acid, myristic or tetradecanoic acid, palmitic or hexadecanoic acid, stearic or octadecanoic acid, arachidic or eicosanoic acid, and behenic or docosanoic acid.

In alternative embodiments, of the present invention, the fatty acid of (2) is selected from the unsaturated fatty acid group comprising oleic acid, linoleic acid, linolenic acid, arachidonic acid, palmitoleic acid, eicosapentaenoic acid, docosahexaenoic acid, and erucic acid.

Furthermore, the thionyl halide of (3) is selected from the group consisting of fluorine, chlorine, bromine, and iodine, the preferred method using chlorine or bromine.

The above reaction proceeds under conditions of heat ranging between from about 35° C. to about 50° C. and stirring over a period from about 0.5 hours to about 2 hours during which time the gases sulfur dioxide and acidic gas, wherein the acidic gas species is dependent on the species of thionyl halide employed, are evolved. Preferably, the reaction proceeds at 45° C. for 1.5 hours.

Step 2 of Scheme 1 entails the neutralization of the carboxylic acid of the amino acid portion through the addition of an inorganic base. The inorganic base is selected from the group comprising sodium hydroxide, potassium hydroxide, lithium hydroxide, ammonium hydroxide, sodium carbonate. Preferred inorganic bases for the purposes of the present invention are sodium hydroxide and potassium hydroxide.

Neutralization, as described above, is followed by the evaporation of water, resulting in the isolation of the corresponding salt. For example, using the amino acid, Arginine and the inorganic base potassium hydroxide, results in the production of the potassium Arginine salt.

Step 3 of Scheme 1 involves the drop wise addition of the prepared acyl halide (4) to the amino acid salt (6) in a cooled flask and subsequent purification by two rounds of distillation to yield the desired anhydride compound (1), the anhydride compound being an amino acid-fatty acid compound of the present invention.

In various embodiments, according to the aforementioned, using the saturated fatty acids, a number of compounds are produced; examples include, but are not limited to: 2-amino-3-methylbutanoic butyric anhydride, 2-amino-3-methylpentanoic hexanoic anhydride, 2,4-diamino-4-oxobutanoic octanoic anhydride, 2,4-diamino-4-oxobutanoic decanoic anhydride, 2-amino-5-guanidinopentanoic dodecanoic anhydride, 2,6-diaminohexanoic tetradecanoic anhydride, 2-amino-5-guanidinopentanoic palmitic anhydride, 2-amino-4-methylpentanoic stearic anhydride, 2-aminopropanoic icosanoic anhydride, and 2-aminoacetic docosanoic anhydride.

In additional embodiments, according to the aforementioned, using the unsaturated fatty acids, a number of compounds are produced; examples include, but are not limited to: 2-aminopropanoic (7Z,10Z)-hexadeca-7,10-dienoic anhydride, 2,5-diamino-5-oxopentanoic oleic anhydride, 2,4-diamino-4-oxobutanoic (9Z,12Z,15Z)-octadeca-9,12,15-trienoic anhydride, 2-aminoacetic (5Z,8Z,11Z,14Z)-icosa-5,8,11,14-tetraenoic anhydride, 2-amino-5-guanidinopentanoic (Z)-hexadex-9-enoic anhydride, 2-amino-3-methylpentanoic (5Z,8Z,11Z,14Z,17Z)-icosa-5,8,11,14,17-pentaenoic anhydride, 2-amino-4-methylpentanoic (4Z,7Z,10Z,13Z,16Z,19Z)-docosa-4,7,10,13,16,19-hexenoic anhydride, and 2-amino-3-methylbutanoic (Z)-docos-13-enoic anhydride.

The following examples illustrate specific amino acid-fatty acid anhydrides and routes of synthesis thereof. One of skill in the art may envision various other combinations within the scope of the present invention, considering examples with reference to the specification herein provided.

EXAMPLE 1

2-amino-3-methylbutanoic butyric anhydride

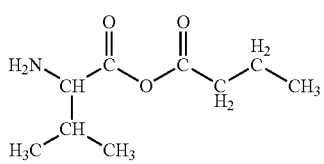

In a dry 2-necked, round bottomed flask, equipped with a magnetic stirrer and fixed with a separatory funnel, containing 8.75 ml (120 mmol) of thionyl chloride, and a water condenser, is placed 9.05 ml (100 mmol) of butanoic acid. Addition of the thionyl chloride is completed with heating to about 40° C. over the course of about 30 minutes. When addition of the thionyl chloride is complete the mixture is heated and stirred for an additional 30 minutes. The water condenser is then replaced with a distillation side arm condenser and the crude mixture is distilled. The crude distillate in the receiving flask is then fractionally distilled to obtain the acyl chloride, butyryl chloride.

Separately, in a single-necked, round bottomed flask, equipped with a magnetic stirrer, 5.86 g (50 mmol) of Valine is dissolved in 200 ml of water. To this is added 55 ml of 1M sodium hydroxide with vigorous stirring, until heat production ceases. At this point the water is removed by evaporation to yield the carboxylate salt, sodium 2-amino-3-methylbutanoate, shown below.

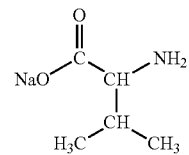

Finally, in a dry 2-necked, round bottomed flask, fixed with a separatory funnel, containing 6.39 g (60 mmol) of the prepared butyryl chloride, and side arm water condenser fixed with a dry receiving flask, is placed 9.18 g (66 mmol) of sodium 2-amino-3-methylbutanoate. The round bottomed flask is placed in an ice bath and the butyryl chloride is added drop wise. After addition is completed the mixture is shaken and the ice bath is replaced by a heating mantle. The flask is then heated until no more solution is dropping into the receiving flask. This crude distillate is then further fractionally distilled to yield 2-amino-3-methylbutanoic butyric anhydride.

EXAMPLE 2

2-amino-3-methylpentanoic hexanoic anhydride

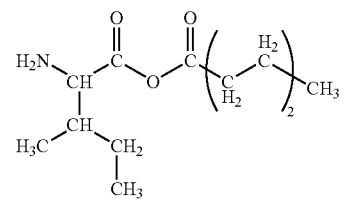

In a dry 2-necked, round bottomed flask, equipped with a magnetic stirrer and fixed with a separatory funnel, containing 6.97 ml (90 mmol) of thionyl bromide, and a water condenser, is placed 5.68 ml (45 mmol) of hexanoic acid. Addition of the thionyl bromide is completed with heating to about 50° C. over the course of about 50 minutes. When addition of the thionyl bromide is complete the mixture is heated and stirred for an additional hour. The water condenser is then replaced with a distillation side arm condenser and the crude mixture is distilled. The crude distillate in the receiving flask is then fractionally distilled to obtain the acyl bromide, hexanoyl bromide.

Separately, in a single-necked, round bottomed flask, equipped with a magnetic stirrer, 6.56 g (50 mmol) of Isoleucine is dissolved in 200 ml of water. To this is added 55 ml of 1M sodium hydroxide with vigorous stirring, until heat production ceases. At this point the water is removed by evaporation to yield the carboxylate salt, sodium 2-amino-3-methylpentanoate, shown below.

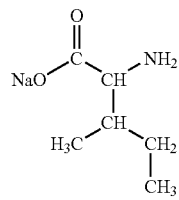

Finally, in a dry 2-necked, round bottomed flask, fixed with a separatory funnel, containing 10.81 g (60 mmol) of the prepared hexanoyl bromide, and side arm water condenser fixed with a dry receiving flask, is placed 11.03 g (72 mmol) of sodium 2-amino-3-methylpentanoate. The round bottomed flask is placed in an ice bath and the hexanoyl bromide is added drop wise. After addition is completed the mixture is shaken and the ice bath is replaced by a heating mantle. The flask is then heated until no more solution is dropping into the receiving flask. This crude distillate is then further fractionally distilled to yield 2-amino-3-methylpentanoic hexanoic anhydride.

EXAMPLE 3

2-amino-5-guanidinopentanoic dodecanoic anhydride

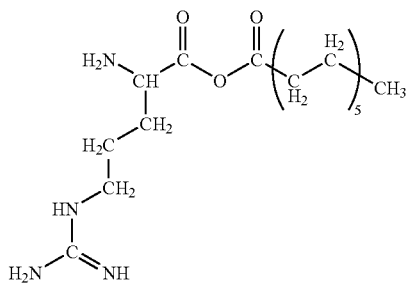

In a dry 2-necked, round bottomed flask, equipped with a magnetic stirrer and fixed with a separatory funnel, containing 5.85 ml (80 mmol) of thionyl chloride, and a water condenser, is placed 10.02 g (50 mmol) of dodecanoic acid. Addition of the thionyl chloride is completed with heating to about 45° C. over the course of about 40 minutes. When addition of the thionyl chloride is complete the mixture is heated and stirred for an additional 50 minutes. The water condenser is then replaced with a distillation side arm condenser and the crude mixture is distilled. The crude distillate in the receiving flask is then fractionally distilled to obtain the acyl chloride, dodecanoyl chloride.

Separately, in a single-necked, round bottomed flask, equipped with a magnetic stirrer, 10.45 g (60 mmol) of Arginine is dissolved in 300 ml of water. To this is added 78 ml of 1M ammonium hydroxide with vigorous stirring, until heat production ceases. At this point the water is removed by evaporation to yield the carboxylate salt, ammonium 2-amino-5-guanidinopentanoate, shown below.

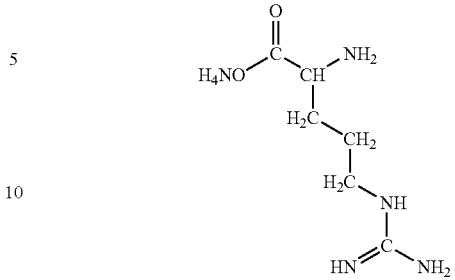

Finally, in a dry 2-necked, round bottomed flask, fixed with a separatory funnel, containing 15.31 g (70 mmol) of the prepared dodecanoyl chloride, and side arm water condenser fixed with a dry receiving flask, is placed 16.06 g (84 mmol) of ammonium 2-amino-5-guanidinopentanoate. The round bottomed flask is placed in an ice bath and the dodecanoyl chloride is added drop wise. After addition is completed the mixture is shaken and the ice bath is replaced by a heating mantle. The flask is then heated until no more solution is dropping into the receiving flask. This crude distillate is then further fractionally distilled to yield 2-amino-5-guanidinopentanoic dodecanoic anhydride.

EXAMPLE 4

2-amino-4-methylpentanoic stearic anhydride

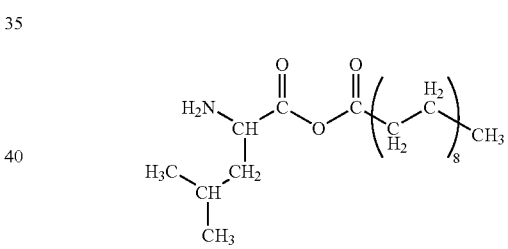

In a dry 2-necked, round bottomed flask, equipped with a magnetic stirrer and fixed with a separatory funnel, containing 4.81 ml (66 mmol) of thionyl chloride, and a water condenser, is placed 15.65 g (55 mmol) of stearic acid. Addition of the thionyl chloride is completed with heating to about 45° C. over the course of about 40 minutes. When addition of the thionyl chloride is complete the mixture is heated and stirred for an additional 45 minutes. The water condenser is then replaced with a distillation side arm condenser and the crude mixture is distilled. The crude distillate in the receiving flask is then fractionally distilled to obtain the acyl chloride, stearoyl chloride.

Separately, in a single-necked, round bottomed flask, equipped with a magnetic stirrer, 7.87 g (60 mmol) of Leucine is dissolved in 300 ml of water. To this is added 72 ml of 1 M potassium hydroxide with vigorous stirring, until heat production ceases. At this point the water is removed by evaporation to yield the carboxylate salt, potassium 2-amino-4-methylpentanoate, shown below.

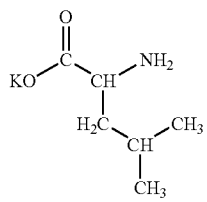

Finally, in a dry 2-necked, round bottomed flask, fixed with a separatory funnel, containing 21.27 g (70 mmol) of the prepared stearoyl chloride, and side arm water condenser fixed with a dry receiving flask, is placed 13.03 g (77 mmol) of potassium 2-amino-4-methylpentanoate. The round bottomed flask is placed in an ice bath and the stearoyl chloride is added drop wise. After addition is completed the mixture is shaken and the ice bath is replaced by a heating mantle. The flask is then heated until no more solution is dropping into the receiving flask. This crude distillate is then further fractionally distilled to yield 2-amino-4-methylpentanoic stearic anhydride.

EXAMPLE 5

2-aminopropanoic (7Z,10Z)-hexadeca-7,10-dienoic anhydride

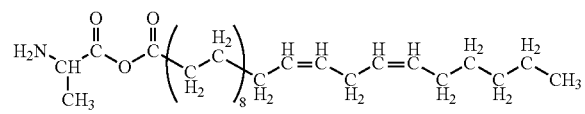

In a dry 2-necked, round bottomed flask, equipped with a magnetic stirrer and fixed with a separatory funnel, containing 9.35 ml (128 mmol) of thionyl chloride, and a water condenser, is placed 24.90 ml (80 mmol) of linoleic acid. Addition of the thionyl chloride is completed with heating to about 40° C. over the course of about 40 minutes. When addition of the thionyl chloride is complete the mixture is heated and stirred for an additional 50 minutes. The water condenser is then replaced with a distillation side arm condenser and the crude mixture is distilled. The crude distillate in the receiving flask is then fractionally distilled to obtain the acyl chloride, (9Z,12Z)-octadeca-9,12-dienoyl chloride.

Separately, in a single-necked, round bottomed flask, equipped with a magnetic stirrer, 5.34 g (60 mmol) of Alanine is dissolved in 200 ml of water. To this is added 78 ml of 1M ammonium hydroxide with vigorous stirring, until heat production ceases. At this point the water is removed by evaporation to yield the carboxylate salt, ammonium 2-aminopropanoate, shown below.

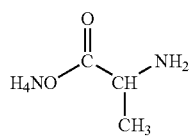

Finally, in a dry 2-necked, round bottomed flask, fixed with a separatory funnel, containing 17.93 g (60 mmol) of the prepared (9Z,12Z)-octadeca-9,12-dienoyl chloride, and side arm water condenser fixed with a dry receiving flask, is placed 7.64 g (72 mmol) of ammonium 2-aminopropanoate. The round bottomed flask is placed in an ice bath and the (9Z, 12Z)-octadeca-9,12-dienoyl chloride is added drop wise. After addition is completed the mixture is shaken and the ice bath is replaced by a heating mantle. The flask is then heated until no more solution is dropping into the receiving flask. This crude distillate is then further fractionally distilled to yield 2-aminopropanoic (7Z,10Z)-hexadeca-7,10-dienoic anhydride.

Thus while not wishing to be bound by theory, it is understood that reacting an amino acid or derivative thereof with a fatty acid or derivative thereof to form an anhydride can be used enhance the bioavailability of the amino acid or derivative thereof by improving stability of the amino acid and by increasing solubility and absorption. Furthermore, it is understood that, dependent upon the specific fatty acid, for example, saturated fatty acids form straight chains allowing mammals to store chemical energy densely, or derivative thereof employed in the foregoing synthesis, additional fatty acid-specific benefits, separate from the amino acid substituent, will be conferred.

EXTENSIONS AND ALTERNATIVES

In the foregoing specification, the invention has been described with a specific embodiment thereof; however, it will be evident that various modifications and changes may be made thereto without departing from the broader spirit and scope of the invention.

What is claimed is:

1. A compound having the general structure:

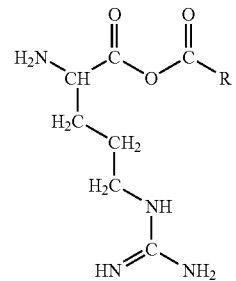

wherein R is selected from the group consisting of alkanes and alkenes;
said alkanes and alkenes having from 3 to 21 carbons.

2. The compound according to claim 1 wherein R is an alkane having 3 to 5 carbons.

3. The compound according to claim 1 wherein R is an alkane having 7 to 9 carbons.

4. The compound according to claim 1 wherein R is an alkane having 11 to 13 carbons.

5. The compound according to claim 1 wherein R is an alkane having 15 to 17 carbons.

6. The compound according to claim 1 wherein R is an alkane having 19 to 21 carbons.

7. The compound according to claim 1 wherein R is an alkene having at least one carbon-carbon double bond, comprising 3 to 5 carbons.

8. The compound according to claim 1 wherein R is an alkene having at least one carbon-carbon double bond, comprising 7 to 9 carbons.

9. The compound according to claim 1 wherein R is an alkene having at least one carbon-carbon double bond, comprising 11 to 13 carbons.

10. The compound according to claim 1 wherein R is an alkene having at least one carbon-carbon double bond, comprising 15 to 17 carbons.

11. The compound according to claim 1 wherein R is an alkene having at least one carbon-carbon double bond, comprising 17 to 21 carbons.

12. The compound of claim 11 having a molecular weight of between about 450 and about 495.

13. A compound having the general structure:

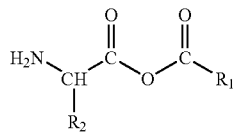

wherein $R_1$ is selected from the group consisting of alkanes and alkenes;
wherein $R_2$ is selected from the group consisting of hydrogen, methyl, isopropyl, isobutyl, sec butyl, acetylamide, propylamide, and butyl-1-amine;
said alkanes and alkenes having from 3 to 21 carbons.

14. The compound according to claim 13 wherein $R_1$ is an alkane having 3 to 5 carbons.

15. The compound according to claim 13 wherein $R_1$ is an alkane having 7 to 9 carbons.

16. The compound according to claim 13 wherein $R_1$ is an alkane having 11 to 13 carbons.

17. The compound according to claim 13 wherein $R_1$ is an alkane having 15 to 17 carbons.

18. The compound according to claim 13 wherein $R_1$ is an alkane having 19 to 21 carbons.

19. The compound according to claim 13 wherein $R_1$ is an alkene having at least one carbon-carbon double bond, comprising 3 to 5 carbons.

20. The compound according to claim 13 wherein $R_1$ is an alkene having at least one carbon-carbon double bond, comprising 7 to 9 carbons.

21. The compound according to claim 13 wherein $R_1$ is an alkene having at least one carbon-carbon double bond, comprising 11 to 13 carbons.

22. The compound according to claim 13 wherein $R_1$ is an alkene having at least one carbon-carbon double bond, comprising 15 to 17 carbons.

23. The compound according to claim 13 wherein $R_1$ is an alkene having at least one carbon-carbon double bond, comprising 17 to 21 carbons.

* * * * *